United States Patent
Corzani et al.

(10) Patent No.: US 6,248,202 B1
(45) Date of Patent: Jun. 19, 2001

(54) PROCESS FOR MANUFACTURING INDIVIDUAL LAYERED STRUCTURES COMPRISING PARTICULATE MATERIAL, AND LAYERED STRUCTURES THEREFROM

(75) Inventors: Italo Corzani, Chieti (IT); Michael Divo, Friedrichsdorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/319,471

(22) PCT Filed: Nov. 20, 1997

(86) PCT No.: PCT/US97/21813

§ 371 Date: Jun. 4, 1999

§ 102(e) Date: Jun. 4, 1999

(87) PCT Pub. No.: WO98/24620

PCT Pub. Date: Jun. 11, 1998

(30) Foreign Application Priority Data

Dec. 4, 1996 (EP) .................................................. 96119425

(51) Int. Cl.[7] .............................. B32B 31/00; B32B 5/16; B32B 7/14; B32B 31/08; A61F 13/15

(52) U.S. Cl. .......................... 156/270; 156/88; 156/251; 156/256; 156/265; 156/268; 156/269; 156/276; 156/325; 156/322; 156/308.02; 156/270; 156/301; 156/302; 156/324; 427/284; 604/359; 604/368; 604/378; 604/385.01

(58) Field of Search .................... 156/88, 251, 256, 156/264, 265, 268, 269, 276, 325, 322, 308.2, 270, 301, 302, 324; 604/359, 368, 378, 385.01; 427/284

(56) References Cited

U.S. PATENT DOCUMENTS

| | | | |
|---|---|---|---|
| 2,619,089 | 11/1952 | Swartz | 604/365 |
| 4,715,918 | 12/1987 | Lang | 156/273.1 |
| 4,960,477 | 10/1990 | Mesek | 156/209 |

FOREIGN PATENT DOCUMENTS 1 462 787 * 1/1977 (GB).
94/01069 1/1994 (WO).

* cited by examiner

Primary Examiner—Linda Gray
(74) Attorney, Agent, or Firm—Matthew P. Fitzpatrick; Kevin C. Johnson (57) ABSTRACT

A process for manufacturing individual layered structures and the structures themselves. A continuous layered structure is provided. The continuous layered structure has designated cutting regions and includes a particulate material between the layers. At least one of the layers is permeable to liquids. A thermoplastic material in liquid state is applied to the continuous layered structure over at least part of the designated cutting regions to provide the designated cutting regions with a joining means. The thermoplastic material is made of natural or synthetic polymers, or mixtures thereof. The thermoplastic material has a softening point, as measured according to the ASTM Method E 28-67, lower than 120° C.; a viscosity at 130° C. lower than 0.05 Pa.s; and a temperature range in which the viscosity changes between 0.05 Pa.s and 0.35 Pa.s which is greater than 5° C. The thermoplastic material is allowed to set. The continuous layered structure is cut in the designated cutting regions to provide individual layered structures.

27 Claims, 3 Drawing Sheets

PROCESS FOR MANUFACTURING INDIVIDUAL LAYERED STRUCTURES COMPRISING PARTICULATE MATERIAL, AND LAYERED STRUCTURES THEREFROM

FIELD OF THE INVENTION

The present invention relates to a process for manufacturing individual layered structures comprising a particulate material, which process prevents the loss or spillage of the particulate material from the structures, and to layered structures manufactured according to this process. Preferably, the individual layered structures comprise absorbent fibrous layers and can be used as absorbent elements in disposable absorbent articles such as absorbent articles for incontinent adults, babies' nappies, sanitary towels, dressings and the like.

BACKGROUND OF THE INVENTION

Disposable absorbent articles are well known and all have absorbent elements for absorbing and retaining body fluids; an absorbent element must be able to acquire liquid rapidly and to distribute it internally so as to prevent leakage and must also have a good capacity to retain the fluids when subjected to the normal pressures of use.

Absorbent elements made mainly of hydrophilic fibrous material such as, for example, pads of cellulose fibres, layers of wadding, or the like generally have satisfactory characteristics as regards their liquid-absorption rate and can distribute the liquid effectively within them but are very ineffective from the point of view of retention when subjected to the normal pressures of use.

The use of absorbent gelling materials in combination with hydrophilic fibres in order to increase the absorption and retention capacities of the absorbent elements is known.

Absorbent gelling materials, commonly known as superabsorbents, are polymers which can swell up and absorb large quantities of liquid, particularly water, or also, to a lesser extent, body fluids.

They also have the particular property that they retain the fluids even under moderate pressure; owing to this characteristic, their use in absorbent elements for disposable absorbent articles has been proposed for some time.

With the use of absorbent gelling materials, it is possible to produce absorbent elements which contain less hydrophilic fibres for a given absorption capacity and which consequently have smaller dimensions, particularly thicknesses, than conventional absorbent elements made of fibres alone.

Absorbent gelling materials are commonly incorporated in particle form within fibrous structures. Structures have been formed in which the fibres and the particles of hydrogelling, absorbent material are disposed in separate, generally very thin, superposed layers or, alternatively, the particles can also be mixed with fibres in one of the fibrous layers.

Many particular forms of layered, absorbent structures of this type, in which the fibrous material is represented by one of more layers of wadding, absorbent paper or non-woven fabric, and in which the particles of absorbent gelling material are incorporated in the structure in various ways, are known in the art.

Different types of particulate materials, other than absorbent gelling material particles, can also be incorporated in layered absorbent structures, such as for example odour control materials in particle or powder form.

Usually a continuous, weblike layered absorbent structure is manufactured, which is subsequently cut in smaller pieces to provide the individual layered absorbent structures to be used as absorbent elements in disposable absorbent articles.

Layered absorbent structures incorporating particulate material can be formed directly on the production line for the absorbent articles in which they are to be incorporated, or, alternatively, they can be produced independently as semi-finished products that are sold and stored separately in form of a continuous web-like structure, e.g. wound in a roll, or otherwise held in a container, and are then fed to the production line.

A common problem with layered absorbent structures incorporating particulate material consists in the effective containment of the particles within the structure in a stable manner, e.g. avoiding that the particles move within the structure and become locally concentrated. The particulate material can also escape from the edges of the layered structure, particularly along the edges where the individual structures are cut from the continuous web-like structure, therefore creating a problem both in the production line and in the final product. known solution for the formation of a layered absorbent structure provides for the use of an adhesive, e.g. of the hot melting type, applied to the entire surface of one of the fibrous layers with the dual purpose of bonding the two fibrous layers together and simultaneously fixing the particles of e.g. absorbent gelling material and/or odour control material between them.

The use of an adhesive may, however, affect the characteristics both of the fibrous layer to which the adhesive is applied, and of the particulate material which come into contact with the adhesive.

In general, therefore, it is necessary not to use an excessive quantity of adhesive and consequently the possibility of the loss of particulate material from the edges of the layered structure cannot be completely eliminated.

Different solutions to the problem of the loss of particulate material along the longitudinal edges of a continuous, web-like layered absorbent structure are known, by longitudinal edges being meant the edges of the layered structure that are parallel to the direction of formation of the structure itself.

For example, the continuous, web-like, layered absorbent structure can be completely surrounded with a layer of wadding, or, alternatively, the structure can be provided by means of a single layer of fibrous material on which the adhesive and the particulate material are distributed only on a central longitudinal strip and subsequently the two side portions are folded so that they partially overlap approximately along the longitudinal axis, and are joined e.g. by means of adhesive.

In International Patent Applications WO 94/01069 and WO 95/17868 by Procter & Gamble Company continuous, web-like, thin, layered absorbent structures containing absorbent gelling material for use as absorbent elements in disposable absorbent articles are described. Such layered absorbent structures are formed by at least two fibrous layers comprising between them a layer of particles of absorbent gelling material, the two fibrous layers being joined together by particles of thermoplastic, polymeric, organic material in finely divided solid form distributed and mixed with the absorbent gelling material, and by two lines of adhesive disposed along the longitudinal edges of the structure.

While the above described layered structures do not have the problem of loss of particulate material along the longitudinal edges, they still have a problem of loss or spillage of particles when they are cut transversely relative to the longitudinal direction in the production line in order to form the individual layered absorbent structures that are to be incorporated as absorbent elements in the absorbent articles. Not only in fact the transverse cuts open the layered structure, therefore exposing the particulate material comprised therebetween, but the cutting action itself tends to break the particles with formation of powders and, which is more likely to occur in the layered absorbent structures described in the two above mentioned international applications, it can also break the bonding points created by the melted polymeric material between the particles and the fibrous layers. The problem of the loss of particulate material along the cut edges is therefore enhanced by these effects.

U.S. Pat. No. 4,715,918 by Kimberly-Clark Corporation and U.S Pat. No. 4,646,510 by Acumeter Lab. Inc., and European Patent EP-B-22792 by Beghin Say SA describe layered structures with particles embedded within two fibrous layers and confined in so called pockets or pouches which are created by the two fibrous layers joined by means e.g. of adhesive or fibre entanglement. The particles are to be selectively deposited on the substrate only on predetermined zones in order to form the pockets or pouches. These methods are capable of achieving a structure sealed both in longitudinal and in transverse direction, but are rather complex and are not suitable to produce pre-formed laminated structures that are to be subsequently fed to a production line and cut at predetermined intervals to form the individual layered absorbent structures.

It is therefore an object of the present invention to provide a process for manufacturing individual layered structures comprising a particulate material, which process prevents the loss or spillage of particulate material from the structures incorporating such material, particularly during the cutting step by which the individual layered structures are cut from a larger layered structure, e.g. a continuous, web-like layered structure.

It is a further object of the present invention to provide such a process that is applicable both to layered structures that are formed directly on the production line for the articles in which they are to be incorporated, and to continuous, web-like, layered structures that are produced as semi-finished intermediate products and are intended to be later fed to the production line.

It is still a further object of the present invention to provide individual layered structures that comprise a particulate material between containing layers that do not have the problem of loss or spillage of the particulate material from the edges thereof.

SUMMARY OF THE INVENTION

The present invention relates to a process for manufacturing individual layered structures comprising the steps of:
a) providing a continuous web-like layered structure having designated cutting regions and comprising a particulate material contained between containing layers, at least one of the layers being permeable to liquids;
b) applying a thermoplastic material in liquid form to the continuous web-like layered structure over at least part of the designated cutting regions, so that the thermoplastic material provides with a joining means the containing layers in at least part of the designated cutting regions,
c) allowing the wax composition to set, and
d) cutting the continuous weblike layered structure in the designated cutting regions to provide the individual layered structures.

The invention further relates to individual layered structures obtainable by this process and cut from a larger structure, which comprise a thermoplastic material applied along at least part of the cut, the thermoplastic material being capable of providing the containing layers with joining means in the region of at least part of the cut where it is applied.

BRIEF DESCRIPTION OF THE DRAWINGS

While the specification concludes with claims particularly pointing out and distinctly claiming the present invention, it is believed that the present invention will be better understood from the following description in conjunction with the following drawings:

DETAILED DESCRIPTION OF THE INVENTION

The invention relates to individual layered structures that are cut from a larger structure and that comprise a particulate material within containing layers, at least one of which layers is liquid permeable, that are joined along the cut so as to prevent loss or spillage of the particulate material from the edges thereof. The invention further relates to a method for manufacturing said structures from a continuous, web-like, layered structure. In a preferred embodiment, the individual layered structures comprise fibrous layers that are preferably liquid absorbent. The individual layered structures of the present invention will be described herein in relation to their use as absorbent elements in disposable absorbent articles, but they can be used for different purposes, for example as an absorbent structure for a cleaning article.

Disposable absorbent articles are intended to be articles that are worn by the user in direct contact with the body; their purpose is to absorb body fluids and they are then thrown away after a single use.

The individual layered structures of the present invention can constitute integrally the absorbent element of a disposable absorbent article, or they can be comprised therein as part of the absorbent element, or in any case they can constitute an element of a disposable absorbent article.

Disposable absorbent articles, such as for example sanitary napkins, pantiliners, incontinent pads, or diapers, typically comprise a fluid pervious topsheet, a fluid impervious backsheet, that can optionally be water vapour and/or gas pervious, and an absorbent element comprised therebetween.

The term "layered", as used herein, indicates any structure in which layers containing particulate material are recognizable from layers that substantially do not comprise particulate material. This comprises structures in which the containing layers and the particulate material are disposed in separate, superposed layers or, alternatively, structures in which the particulate material is embedded in a given position within the thickness of a single layer, e.g. a fibrous layer, for example in correspondence of the centre of the layer, in order to prevent particulate material from escaping from one or both major flat surfaces of the layered structure.

The term "cutting region", as used herein, indicates an area of one of the major flat surfaces of the continuous web-like layered structure that entirely comprises a cutting line, i.e. the line where the cut is to be made in order to obtain an individual web-like layered structure from the continuous weblike layered structure. In case straight cutting lines only are involved, the cutting region is typically an area delimited by two approximately straight lines both parallel to the cutting line, laying on either sides of the cutting line.

The structure can also comprise non fibrous containing layers, for example a polymeric film layer, provided that at least one of the containing layers is liquid permeable.

The process of the present invention for manufacturing individual layered absorbent structures, and the individual layered absorbent structures therefrom, will be herein described with reference to a continuous, web-like, layered absorbent structure which is similar to the thin layered absorbent structures described in the two above cited international applications WO 94/1069 and WO 95/17868.

Figure 1:
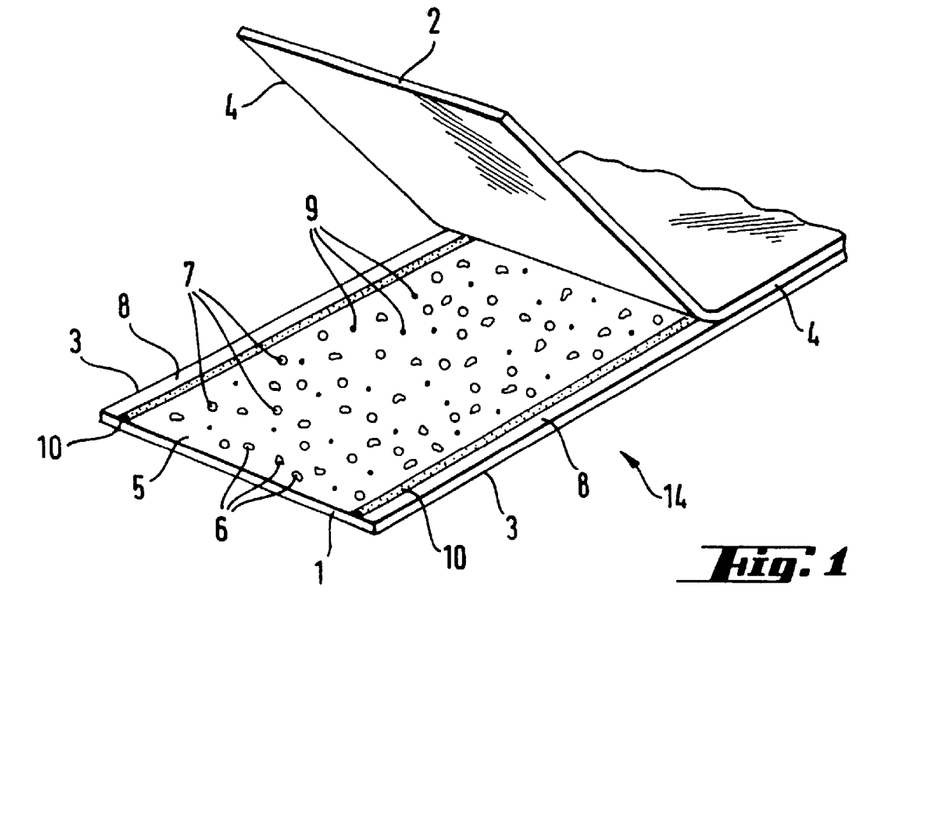
FIG. 1 is a perspective view of a continuous, web-like, layered structure that can be employed to form individual layered structure according to the present invention.

FIG. 1 shows a continuous, web-like, layered absorbent structure 14 with one of the layers partially raised to show its construction more clearly.

In FIG. 1 it is possible to distinguish a first fibrous layer 1 and a second fibrous layer 2 in the form of two continuous strips of the same width, which are superposed so that their respective longitudinal edges 3 and 4 coincide; the fibrous layers constitute the containing layers and can be made of various materials such as, for example, paper, wadding, or non-woven fabric; they are preferably made of dry-formed layers, generally referred to as "air laid" layers, of short cellulose fibres having a basic weight of between 20 g/m$^2$ and 150 g/m$^2$.

Alternatively, the two fibrous layers can be made of different materials, for example the second fibrous layer 2 may consist of a dry-formed mixture of cellulose fibres and bicomponent polyethylenelpolypropylene fibres, such as, for example, those sold by Danaklon a/s of Varde, Denmark, as AL-Thermal B and AL-Thermal C.

Between the two containing fibrous layers 1 and 2 there is an intermediate layer 5 of particulate material made of a mixture of particles of hydrogelling, absorbent material 6, particles of odour control material 9 and a thermoplastic, polymeric, organic material in finely divided solid form, preferably in form of particles 7; the width of the said intermediate layer 5 is less than that of the outer two fibrous layers 1 and 2 which extend beyond the intermediate layer 5 laterally forming two longitudinal edge portions 8 at their respective longitudinal edges 3 and 4.

The longitudinal direction typically corresponds to the direction of formation of the continuous, web-like layered absorbent structure 14.

The two outer fibrous layers 1 and 2 are bonded together in the central region in which the intermediate layer 5 is present by the application of heat and moderate pressure to melt the particles 7 of thermoplastic, polymeric, organic material present in the intermediate layer 5, mixed with the particles 6 of hydrogelling, absorbent material, and 9 of odour control material.

The bond between the fibrous layers 1 and 2 is generated by the melting of the individual particles 7 of thermoplastic polymeric, organic material; as it melts, the polymeric material forms "bridges" connecting directly the fibrous layers 1 and 2 and/or also comprising particles 6 of absorbent gelling material, and particles 9 of odour control material.

It has to be noted that in the finished product the term "particulate material" identifies only the particles 6 of absorbent gelling material and 9 of odour control material, since the thermoplastic polymeric material after the melting step is no more in form of particles 7.

The overall surface area of the bond points represents a small fraction of the surface area of the fibrous layers 1 and 2 and of the particles of hydrogelling, absorbent material and odour control material, the characteristics of which thus remain almost unchanged.

Two continuous lines 10 of adhesive are also applied to the two sides of the intermediate layer 5 on the longitudinal edge regions 8 of the two outer fibrous layers 1 and 2 so as to prevent the particulate material, i.e. particles of hydrogelling, absorbent material 6 and of odour control material 9 from escaping from the longitudinal edges of the layered structure, which correspond to the superposed edges 3 and 4 of the two fibrous layers, and also to reinforce the connection between the fibrous layers themselves.

The containing layers and the particulate material can be alternatively bonded together by different means, other than the thermoplastic polymeric material in finely divided solid form, e.g. in form of particles 7 and the continuous lines of adhesive 10 described herein; for example, a sprayed layer of adhesive can replace at least the thermoplastic polymeric material in finely divided solid form.

The absorbent gelling material, which is preferably distributed in the form of particles 6, may be made of inorganic or organic substances such as cross-linked polymers, all known from the prior art. The odour control material can be any suitable odour control material known in the art, for example it can be constituted by particles of zeolite and silica.

The average dimensions of the particles 6 and 9, given as a weighted average of the smallest dimensions of the individual particles, can be between 50 microns and 1500 microns, preferably between 100 microns and 800 microns.

The quantity of the absorbent gelling material 6 in the intermediate layer 5 can range from 20 g/m$^2$, up to 600 g/m$^2$. The quantity of odour control material 9 can be between 40 g/m$^2$ and 200 g/m$^2$.

The thermoplastic, polymeric, organic material in finely divided solid form, e.g. in form of particles 7 has the purpose of bonding the two fibrous layers 1 and 2 together by melting and forming discrete, spaced-apart bond points between the fibres of the two layers. The thermoplastic, polymeric, organic material can also be used in other finely divided solid forms, e.g. in form of fibres.

As explained above, the bridges which form these bond points can involve particles of hydrogelling material and odour control material.

The quantity of thermoplastic, polymeric, organic material in finely divided solid form distributed and mixed with the hydrogeliing, absorbent material can be between 5 g/m$^2$ and 180 g/m$^2$.

The thermoplastic, polymeric, organic material in finely divided solid form can preferably be melted at a temperature such as not to interfere with the characteristics of the other components of the layered structure, i.e. the fibrous layers and the particulate material, namely the hydrogelling, absorbent material and the odour control material. Therefore, the thermoplastic polymeric organic material must have fluidity characteristics such as to enable the necessary bonds to be formed rapidly.

These preferred characteristics can be achieved by a thermoplastic, polymeric, organic material in finely divided solid form having a melt flow index (M.F.I.), evaluated by the ASTM method D 1238-85 under conditions 190/2.16, of at least 25 g/10 min, preferably at least 40 g/10 min, and even more preferably at least 60 g/10 min.

If the layers 1 and 2 are made of a dry-formed short cellulose fibre material, it is preferable to use a thermoplastic, polymeric, organic material composed of particles of high-density polyethylene with maximum dimensions of about 400 microns, characterized by a melt flow index of about 50 g/10 min, of which the quantity distributed is between 12 g/m$^2$ and 90 g/m$^2$.

The continuous, weblike, layered absorbent structure 14 may also be formed by two different fibrous layers or may comprise more than two fibrous layers, and consequently more than one intermediate layer formed by the mixture of particulate material, e.g. particles of hydrogelling, absorbent material and of odour control material, and particles of thermoplastic, polymeric, organic material.

Of course, provided that a particulate material is actually comprised between containing layers, any of the absorbent gelling material, odour control material, or thermoplastic, polymeric, organic material in finely divided solid form comprised in a preferred layered structure made according to the present invention can be in a form which is different from the particulate form. For example, the absorbent gelling material can be in fibrous form, while the odour control material can be comprised as a solution sprayed onto a substrate; the thermoplastic, polymeric, organic material in finely divided solid form can also be in fibrous form, as already mentioned above.

The continuous lines 10 of adhesive disposed between the fibrous layers on the respective longitudinal edge portions prevent the particulate material forming the intermediate layer from escaping from the longitudinal edges of the structure. The structure therefore can be produced separately and stored as it is, for example, as a continuous strip rolled in the form of a roll 11, shown in FIG. 2, which can subsequently be fed to the production line for disposable absorbent articles, for example sanitary napkins, where individual layered absorbent structures 12 are manufactured from the continuous, web-like, absorbent structure 14 in order to be incorporated as absorbent elements in the absorbent articles.

Figure 3:
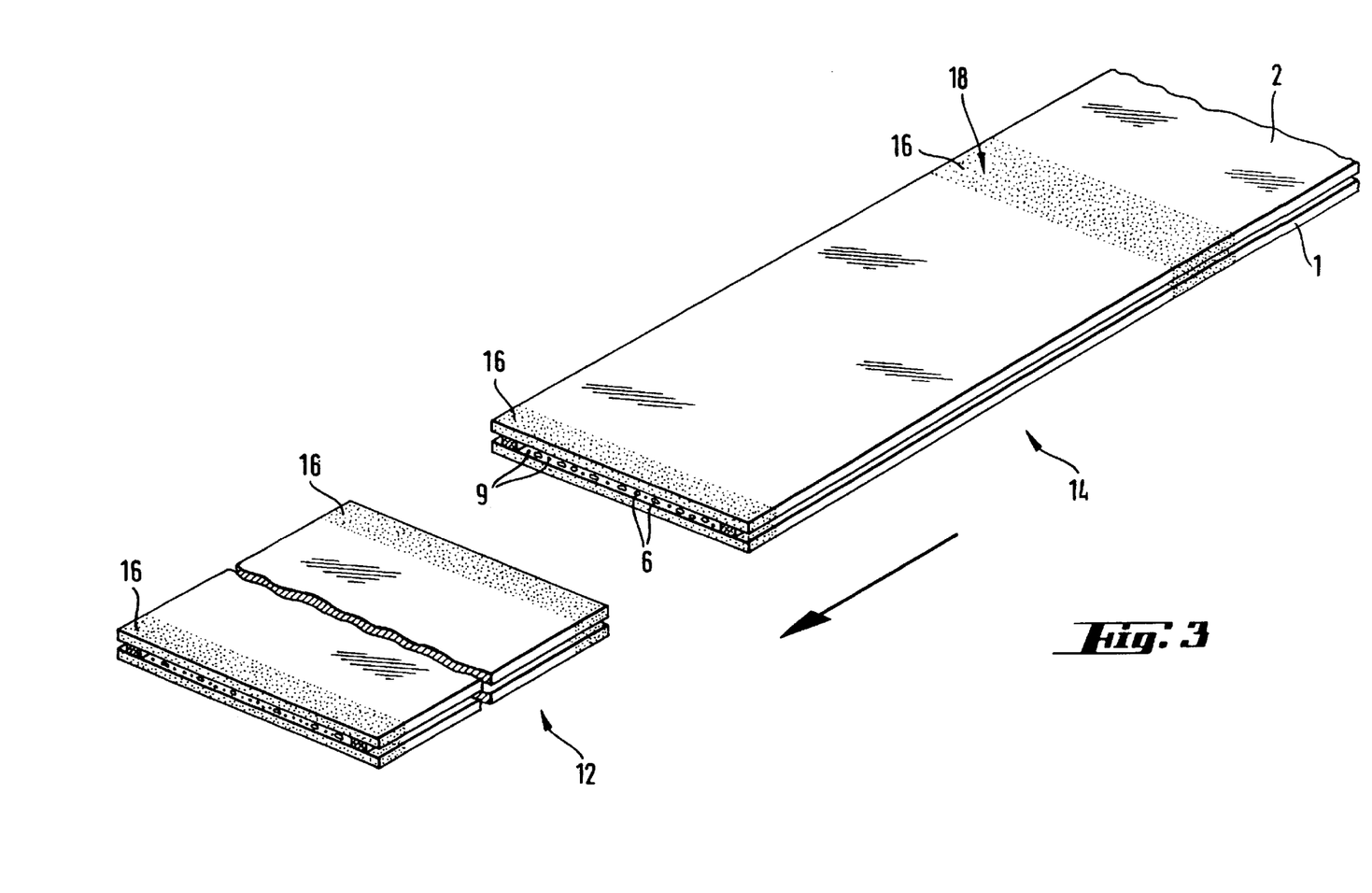
FIG. 3 is a perspective view of an individual layered structure being made from a continuous, web-like layered structure in accordance with the present invention.

As illustrated in FIG. 3, individual layered absorbent structures 12 of the desired length can be cut from a continuous, web-like, layered absorbent structure 14 of the type described above by means of cuts made in designated cutting regions 18 situated at predetermined intervals along the continuous structure 14; as shown in FIG. 3, the cuts are made in a direction transverse to the direction of feeding of the continuous structure 14 to the production line, which is indicated by an arrow and corresponds to the longitudinal direction of the continuous structure 14.

Prior to the cutting step a low molecular weight, natural or synthetic thermoplastic material 16 is applied in liquid state to a surface of the continuous structure 14 over said designated cutting regions 18; the thermoplastic material 16 must be capable of impregnating the continuous structure 14 in its entire thickness, and as it sets after it has been applied, it joins the superimposed fibrous layers 1 and 2 in said designated cutting regions 18, and at the same time entraps the particulate material 6 and 9 which is comprised between the fibrous layers 1 and 2. When the transverse cut is subsequently made in each designated cutting region 18 the particulate material 6, 9 cannot escape from the cut edge of the layered structure, since it is firmly held within the layered structure by the solidified thermoplastic material 16. The thermoplastic material 16 therefore preferably performs a sealing action on the designated cutting region 18 where it is applied.

It is not intended in the scope of the present invention that the thermoplastic material must totally entrap the particulate material comprised in the continuous web-like layered structure 14, but rather that the thermoplastic material constitutes a joining means for the containing layers, entrapping a substantial percentage of the particulate material contained between them and therefore reducing the loss or spillage of particulate material where the cut is subsequently made. A minor loss of particulate material, e.g. through parts of the designated cutting regions where the thermoplastic material is not applied, is within the scope of the present invention.

As shown in FIG. 3, each designated cutting region 18, indicated on the continuous absorbent structure 14 by means of a shading, can have an approximately rectangular form extending over the entire width of the continuous absorbent structure 14 and having a certain length in longitudinal direction.

The length in longitudinal direction of the designated cutting regions 18 where the thermoplastic material 16 has to be applied, and the position of each cut within each designated cutting region 18 must be so arranged and synchronized that each cut occurs preferably in the middle of the respective designated cutting region 18. The surface of the continuous structure 14 interested by the application of the thermoplastic material 16, that corresponds to the surface of each designated cutting region 18, must be kept to a minimum in order to reduce the possible influence of the applied thermoplastic material 16 to the absorbent capacity and to the softness of each resultant individual layered absorbent structure 12, while still performing the intended joining action of the fibrous layers 1 and 2 and the entrapping action of the particulate material comprised therebetween. A suitable length for the designated cutting regions 18 in a continuous structure 14 intended to provide individual layered structures 12 used as absorbent elements in disposable sanitary napkin can be about 2 cm, but this value may be varied by the skilled man according to the dimensions and the thickness of the individual layered structure 12.

The thermoplastic material 16 can be applied in liquid state to the continuous, web-like layered structure 14 at the designated cutting regions 18 in different ways, e.g. by slot coating, or spraying, or curtain coating.

The thermoplastic material 16 can be constituted by any low molecular weight, synthetic or natural thermoplastic polymeric composition having a sufficiently low viscosity in the molten state in order to completely impregnate the full thickness of the continuous, web-like, layered structure 14 in the area where it is to be applied. The thermoplastic material 16 has preferably a softening point sufficiently low so as to avoid possible interactions with the materials that constitute the layered structure 14. The softening point, as measured according to the ASTM Method E 28-67, is preferably lower than 120° C., more preferably lower than 100° C., most preferably lower than 85° C. For individual web-like layered structures used as absorbent cores in disposable absorbent products it is preferred that the softening point of the thermoplastic material 16 is not lower than about 50° C. The viscosity at 130° C. is preferably lower than 0.05 Pa.s, more preferably lower than 0.02 Pa.s, and most preferably lower than 0.01 Pa.s.

The setting time of the thermoplastic material 16 should be fast enough to allow a quick setting after the application of the thermoplastic material 16 to the structure 14. Thermoplastic materials 16 having the preferred characteristics in terms of viscosity and softening point usually have an extremely fast setting time once the temperature of the thermoplastic material 16 drops below the softening point, and this can also affect the capability of the thermoplastic material 16 to impregnate a substrate where it is applied, e.g. the layered structure 14. A suitable measure of the setting time of a thermoplastic material 16 can be expressed in terms of the temperature range in which the viscosity of the thermoplastic material 16 changes from 0.05 Pa.s (liquid state) to 0.35 Pa.s (substantially semi solid state), in the liquid to solid state transition, or vice versa. The higher the temperature range, the lower the setting time of the thermoplastic material 16. According to the present invention, said temperature range should be greater than 5° C., preferably greater than 7° C., more preferably greater than 10° C.

In order to improve the capacity of the thermoplastic material 16 of effectively impregnating the layered structure where it is applied, i.e. the designated cutting regions 18 of the continuous, web-like, layered absorbent structure 14, the temperature at which the thermoplastic material 16 is applied is preferably between 150° C. and 220° C. Preferably, the continuous, web-like, layered absorbent structure 14 is pre-heated prior to the application of the thermoplastic material 16, with any known means, e.g. by means of a stream of hot air, or of infrared heating, or of heated rolls, up to a temperature that, depending on the thickness of the substrate itself, can be preferably not lower than 20° C. below the softening point of the thermoplastic material 16.

The thermoplastic material 16 can be applied in an amount ranging from 10 g/m$^2$ and 120 g/m$^2$, preferably from 35 g/m$^2$ and 85 g/m$^2$, most preferably from 45 g/m$^2$ to 75 g/m$^2$.

Viscosity, setting time, application temperature, and quantity for the thermoplastic material 16, and temperature of pre-heating for the substrate can be varied according to the characteristics of the substrates that constitute the continuous, web-like structure where the thermoplastic material 16 has to be applied, particularly in terms of basis weight and thickness of such substrates, and the right balance among all those different parameters within the preferred ranges can be easily defined by the man skilled in the art.

For example a thicker and heavier substrate will require a thermoplastic material having a lower viscosity at the temperature at which it is applied, and a pre-heating of the substrate up to a higher temperature, as compared to the conditions required by a thinner, lighter substrate.

Any synthetic or natural wax with the preferred values of viscosity, softening point and setting time, expressed as defined above, is preferred as thermoplastic material 16. Microcrystalline naphtenic waxes are usually preferred to paraffinic waxes for the scope of the present invention since they generally have a suitable setting time and are softer in the solid state, thus affecting to a minimum extent the softness of the resultant individual layered structures 12.

Figure 2:
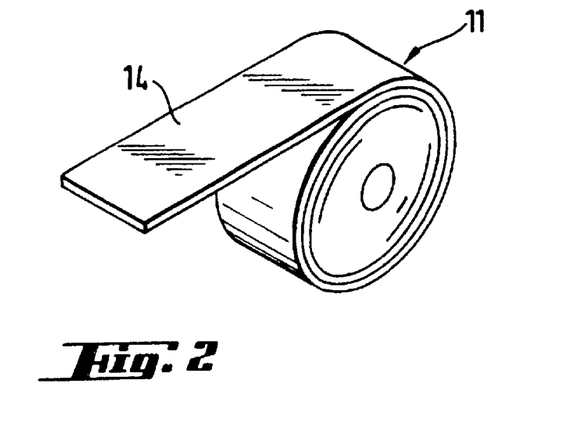
FIG. 2 is a perspective view of a continuous, web-like, layered structure of the type illustrated in FIG. 1, wound in a roll.

In an example of the present invention a continuous, web-like, layered absorbent structure 14 of the type described previously and e.g. wound in a roll as that illustrated in FIG. 2 is fed to a production line of a sanitary napkin, said structure having a width of 70 mm and an overall thickness of 1.5 mm, and comprising:

a first layer formed from a resin bonded air laid web of cellulose fibres 60 g/m$^2$;

an intermediate layer formed by a mixture of 63 g/m$^2$ of particles of absorbent gelling material, 61 g/m$^2$ of particles of zeolite, 88 g/m$^2$ of particles of silica, and 40 g/m$^2$ of particles of polyethylene;

a second layer formed from a resin-bonded air laid web of cellulose fibres 60 g/m$^2$.

The two continuous lines of adhesive comprise two lines of hot-melt adhesive approximately 2 mm in width.

The thermoplastic material 16 is a naphtenic wax sold by Witco Holland under the tradename WITCODUR 263 and having a viscosity at 130° C. of 0.0087 Pa.s, a softening point of about 80° C., and a setting time, expressed as explained above as range of temperature, of 14° C. The wax is applied at designated cutting regions 20 mm long situated at predetermined intervals of about 207 mm along the continuous weblike structure 14, and oriented orthogonally with respect to the direction of feeding, the designated cutting regions extending over the entire width of the continuous web-like structure 14. The wax composition is applied in an amount of 75 g/m$^2$ and at a temperature of 160° C. onto the first layer of the continuous, web-like, layered absorbent structure, the substrate being pre-heated by means of heated rolls up to a temperature of about 70° C.

After setting of the wax composition the continuous, weblike, layered absorbent structure 14 is cut transversely to the direction of feeding in each designated cutting region 18, the cuts being located in the middle of each designated cutting region 18, with respect to the direction of feeding. Individual layered absorbent structures 12 that are 207 mm long are therefore provided and can be subsequently incorporated as absorbent elements in absorbent articles, e.g. sanitary napkins.

In an alternative embodiment of the method of the present invention the designated cutting regions 18 of the continuous, web-like, layered structure 14 can also be heat crimped immediately after the application of the wax composition, and prior or at the same time of the cutting step. Preferably the crimping is performed onto the continuous, web-like layered structure 14 on the same side of the application of the thermoplastic material 16. The crimping helps the thermoplastic material 16 impregnate the containing layers, and at the same time the thermoplastic material 16 itself performs a smoothening action, therefore avoiding possible breaking of the containing layers during the crimping step.

Figure 4:
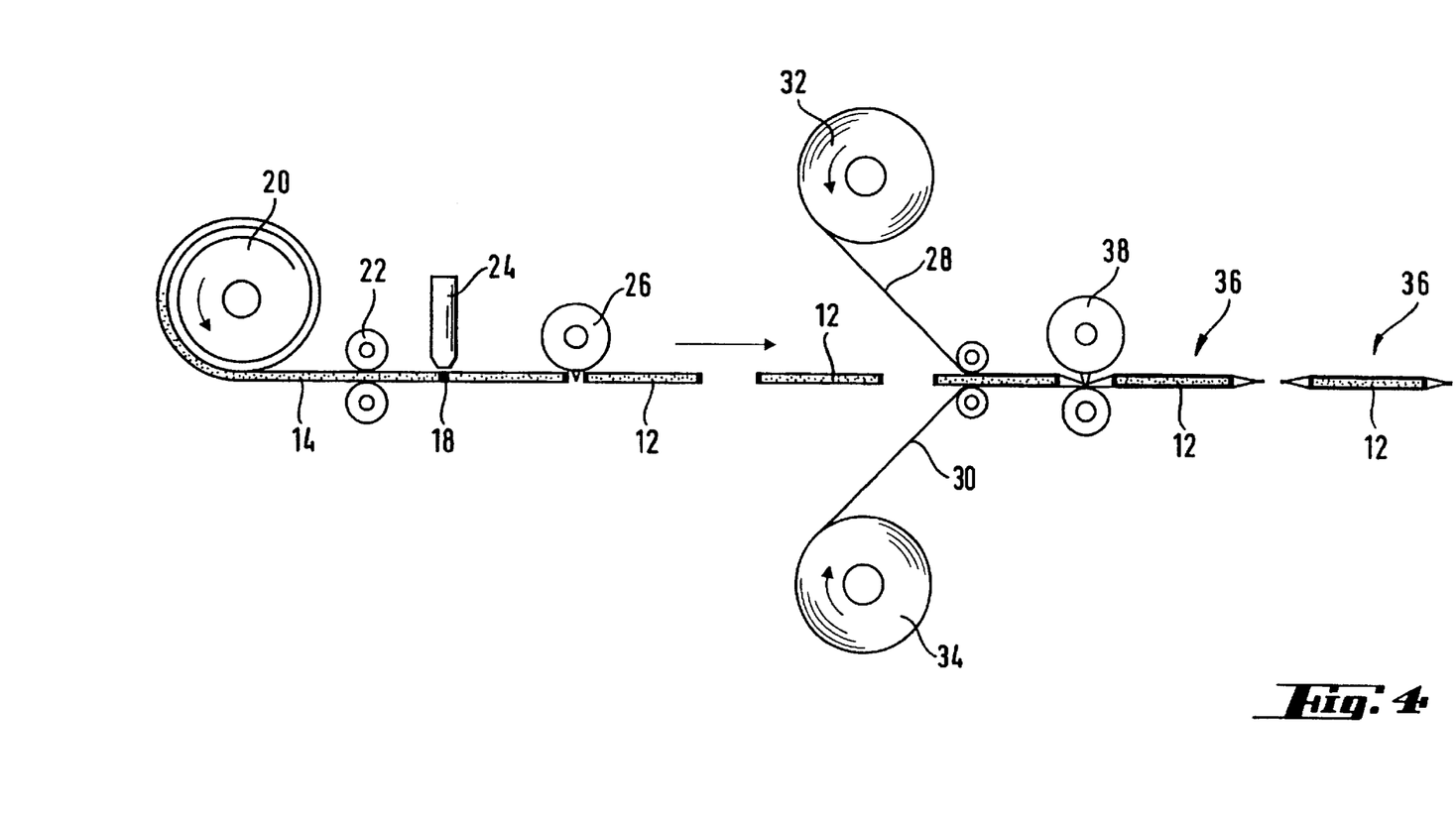
FIG. 4 is a schematic flow diagram of a process for making individual layered absorbent structures and for incorporating them in absorbent articles according to the present invention.

FIG. 4 is a simplified diagram of a process for producing a disposable absorbent article, eg. a sanitary napkin, that uses as absorbent element an individual layered absorbent structure 12 obtainable from a continuous, web-like, layered absorbent structure 14 fed as a semi-finished product.

The reel 20 supplies the continuous, web-like, layered absorbent structure 14 to the production line; the structure 14 is pre-heated by hot rolls 22 and immediately after a thermoplastic material 16 is applied at designated cutting regions 18 by means of an applier 24. The continuous structure 14 is then cut into individual layered absorbent structures 12 at the cutting station 26, and the individual structures 12 are scattered in the direction of the production line and then fed to an assembly station where a fluid pervious topsheet 28 and a fluid impervious backsheet 30 are supplied from reels 32 and 34, respectively. The topsheet 28 and the backsheet 30 incorporate the individual structures 12 therebetween, and are finally joined together and cut along a perimeter at a cutting and sealing station 38 to form sanitary napkins 36 each comprising an individual structure 12.

A crimping station, not shown in FIG. 4, can be incorporated into the production line between the applier 24 and the cutting station 26, or, alternatively, the crimping station can be incorporated into the cutting station, which therefore would perform both actions of cutting and crimping at the same time.

While the process and the product of the present invention have been described in association with a continuous, web-like, layered structure having three distinct layers, it can be also applicable to different continuous layered structures, e.g. to structures having a different number of superimposed layers, or, alternatively, to another known type of C-folded absorbent laminate consisting of a single fibrous layer folded twice on itself and sealed by means of adhesive along the overlapping longitudinal side margins; the particulate material, e.g. absorbent gelling material and odour control material, is comprised therebetween. The particulate material and the superimposed portions of the fibrous layer are bonded together by means of sprayed adhesive. This type of structure is typically made on the production line of a sanitary napkin, rather than being produced as a semi-finished product to be subsequently fed to the production line. It does not have loss or spillage of particulate material along the longitudinal edges, but still has this problem when it is cut in transverse direction in the production line in order to form the individual layered structures that are to be incorporated in the sanitary products.

In an alternative embodiment of the present invention the process can also be used to produce individual layered structures cut from a larger structure by means of longitudinal and transverse cutting lines defining respective designated cutting regions. The individual layered structures can be joined by the previous application of the thermoplastic material over the entire designated cutting regions, i.e. along the entire cut, in both transverse and longitudinal directions.

What is claimed is:

1. A process for manufacturing individual layered structures comprising the steps of:
   a) providing a continuous layered structure, said continuous, layered structure having designated cutting regions and comprising a particulate material between containing layers, at least one of said layers being permeable to liquids;
   b) applying a thermoplastic material in liquid state to said continuous layered structure over at least part of said designated cutting regions, so that said thermoplastic material provides said containing layers in said at least part of said designated cutting regions with a joining means, said thermoplastic material comprises natural or synthetic polymers, or mixtures thereof having the following features:
      a softening point, as measured according to the ASTM Method E 28-67, lower than 120° C.;
      a viscosity at 130° C. lower than 0.05 Pa.s;
      a temperature range in which the viscosity changes between 0.05 Pa.s and 0.35 Pa.s which is greater than 5° C.;
   c) allowing said thermoplastic material to set, and
   d) cutting said continuous layered structure in said designated cutting regions to provide said individual layered structures.

2. A process according to claim 1, wherein said thermoplastic material is a wax composition.

3. A process according to claim 2, wherein said thermoplastic material is a microcrystalline naphtenic wax.

4. A process according to claim 1, wherein said joining means constitute a seal.

5. A process according to claim 1, wherein said containing layers are fibrous layers.

6. A process according to claim 5, wherein said containing layers are absorbent fibrous layers.

7. A process according to claim 1, wherein step a) is done by feeding said continuous layered structure along a given direction and said thermoplastic material is applied to said continuous layered structure at predetermined intervals transversely with respect to said given directions, over the entire width of said continuous layered structure.

8. A process according to claim 1, wherein it further comprises the step of pre-heating said continuous layered structure prior to the application of said thermoplastic material.

9. A process according to claim 8, wherein the temperature of said pre-heating of said continuous layered structure is not lower than 20° C. below the softening point of said thermoplastic material.

10. A process according to claim 1, wherein said thermoplastic material is applied in an amount between 10 g/m² and 120 g/m².

11. A process according to claim 10, wherein said thermoplastic material is applied in an amount between 35 g/m² and 85 g/m².

12. A process according to claim 11, wherein said thermoplastic material is applied in an amount between 45 g/m² and 75 g/m².

13. An individual layered structure comprising a particulate material contained between containing layers, at least one of said layers being permeable to liquids, said individual layered structure being cut from a larger structure and joined along said cut, said individual layered structure being wherein it further comprises a thermoplastic material applied along at least part of said cut, said thermoplastic material providing said containing layers with joining means in the region of said at least part of said cut where it is applied, said thermoplastic material having the following features:
   a softening point, as measured according to the ASTM Method E 28-67, lower than 120° C.;
   a viscosity at 130° C. lower than 0.05 Pa.s;
   a temperature range in which the viscosity changes between 0.05 Pa.s and 0.35 Pa.s which is greater than 5° C.

14. An individual layered structure according to claim 13, wherein said thermoplastic material comprises natural or synthetic polymers, or mixtures thereof.

15. An individual layered structure according to claim 13, wherein said thermoplastic material is a wax composition.

16. An individual layered structure according to claim 15, wherein said thermoplastic material is a microcrystalline naphtenic wax.

17. An individual layered structure according to claim 13, wherein said joining means constitutes a seal.

18. An individual layered structure according to claim 13, wherein said containing layers are fibrous layers.

19. An individual layered structure according to claim 18, wherein said containing layers are absorbent fibrous layers.

20. An individual layered structure according to claim 13, wherein said cut comprises a first pair of opposite side margins and a second pair of opposite side margins oriented substantially transversely with respect to said first pair of opposite side margins, said thermoplastic material being applied along said second pair of opposite side margins.

21. An individual layered structure according to claim 13, wherein it comprises first and second fibrous layers and an intermediate layer comprising a particulate material distributed between said first and second fibrous layers, said intermediate layer also comprising a thermoplastic polymeric material in finely divided solid form, said thermoplastic polymeric material in finely divided solid form bonding said first and second fibrous layers together.

22. An individual layered structure according to claim 21, wherein said first and second fibrous layers extend beyond said intermediate layer laterally forming said first pair of opposite side margins, and in that said first and second fibrous layers are sealed together along said first pair of opposite side margins by means of continuous lines of adhesive.

23. An individual layered structure according to claim 13, wherein said thermoplastic material is applied in an amount between 10 g/m$^2$ and 120 g/m$^2$.

24. An individual layered structure according to claim 23, wherein said thermoplastic material is applied in an amount between between 35 g/m$^2$ and 85 g/m$^2$.

25. An individual layered structure according to claim 24, wherein said thermoplastic material is applied in an amount between 45 g/m$^2$ and 75 g/m$^2$.

26. A disposable absorbent article comprising an absorbent element comprising an individual layered structure as claimed in claim 13.

27. A disposable absorbent article comprising an absorbent element comprising an individual layered structure obtained by a process according to claim 1.

* * * * *